(12) United States Patent
Caprarotta et al.

(10) Patent No.: US 8,585,953 B2
(45) Date of Patent: Nov. 19, 2013

(54) PROCESS FOR PREPARING TABLET POWDER OR POURED COSMETIC PRODUCTS

(75) Inventors: Grazia Anna Caprarotta, Verdello (IT); Marina Guanziroli, Chieve (IT)

(73) Assignee: Color Cosmetics S.R.L., Milan (IT)

( * ) Notice: Subject to any disclaimer, the term of this patent is extended or adjusted under 35 U.S.C. 154(b) by 203 days.

(21) Appl. No.: 12/893,401

(22) Filed: Sep. 29, 2010

(65) Prior Publication Data

US 2012/0025424 A1     Feb. 2, 2012

(30) Foreign Application Priority Data

Jun. 1, 2010 (IT) .............................. MI2010A0993
Jul. 27, 2010 (IT) .............................. MI2010A1381

(51) Int. Cl.
*B29C 39/24* (2006.01)
(52) U.S. Cl.
USPC ...................................................... 264/319
(58) Field of Classification Search
USPC ...................................................... 264/319
See application file for complete search history.

(56) References Cited

U.S. PATENT DOCUMENTS 6,085,759 A * 7/2000 Joulia ............................ 132/293
2009/0041698 A1 * 2/2009 Cabiling et al. ................ 424/69

FOREIGN PATENT DOCUMENTS

EP     0864270 A1      9/1998
EP     1325692 A2      7/2003

OTHER PUBLICATIONS

European Search Report (EP 10 18 2041) dated Mar. 7, 2011.

* cited by examiner

*Primary Examiner* — Yogendra Gupta
*Assistant Examiner* — Robert J Grun
(74) *Attorney, Agent, or Firm* — Novak Druce Connolly Bove + Quigg LLP

(57) ABSTRACT

A new process for preparing tablet powder or poured cosmetic products comprises preparing different cosmetic compounds in a slurry, i.e. "semi-liquids", preparing a premolded container (1) equipped with separating partitions (2) of small height with respect to the total depth of the container (1) and pouring said cosmetic compounds (4) into respective spaces adjacent to the container (1) defined between said partitions (2). Pouring is performed so that at least one of said poured compounds surmounts all the partitions (2) of the container (1). The process continues with the solidification of the poured compounds until forming a unique cosmetic product (6) with adjacent tablets (4) corresponding to the different poured compounds, the extraction of said unique solidified product (6) from the container (1), and its insertion into a final package. The internal partitions (3) of the container (1) may be fixed to the bottom of the container (1) in a permanent or removable manner.

12 Claims, 3 Drawing Sheets

PROCESS FOR PREPARING TABLET POWDER OR POURED COSMETIC PRODUCTS

CROSS-REFERENCE TO RELATED APPLICATIONS

This application claims priority to Italian Patent Application MI2010A001381, filed Jul. 27, 2010, the entirety of which is incorporated herein by reference, and to Italian Patent Application MI2010A000993, filed Jun. 1, 2010.

FIELD OF THE INVENTION

The present invention relates to a process for preparing tablet powder or poured cosmetic products.

BACKGROUND

Methods are known for preparing coloured, tablet cosmetic products, either in the form of powder or poured.

In general, there are two systems to prepare a multicoloured powder cosmetic in the same container, also named godet.

One consists of dosing the single coloured powders into respective cavities laterally adjacent to a metal cylinder equipped with separating partitions. The powders are poured in dosed amounts by means of screws into said cavities and pressed in the cavities themselves by means of respective metal pressing devices exactly shaped as the cavities containing them. Respective pellets are thus obtained which are kept separate from one another by the separating partitions. The tablets are then ejected from the respective cavities and adjacently inserted into a cup, where they are jointed by final pressing by using a compacting mould. A relief or positive-reverse engraving or the like may also be press-imprinted on the product surface.

The number of cavities may vary from two up to more than five, therefore cosmetic products may also be obtained with more than five tablets of different colours and shapes assembled inside the cup itself.

However, such a process is very complex and costly because the metal cylinder in which the partitions are arranged is difficult to be implemented, and extremely fragile because, as a rule, the thickness of the partitions may not exceed 1 mm.

The powder dosing system is also difficult due to the high precision required by the dosages which sometimes are up to 0.5 g and a minimal adhesion of the product to the screws creates an excessive variation in the dosage itself.

The aspect of the compacted product is also little satisfying due to the colour overflows which invade the various sectors.

For this reason, the system currently most used for producing cosmetic products with multicoloured tablets in the same cup is that including pre-forming the single tablets inside the single pre-compacting moulds, ejecting the tablets from the pre-compacting moulds, assembling them in the cup by means of a vacuum transport system, and finally compacting by means of a pressing device. The pressing surface may be machined so as to provide the compacted product with relief, volume and other effects.

This method, which may be used to obtain from two to more than ten tablets in the same cup, is particularly laborious, complex and costly because a single pre-compacting mould is to be made for each tablet, and a pre-compacting and assembling production operation in the cup corresponds to each tablet, without considering that machining the cup results in very precise limits and size restrictions, such as the impossibility to make angles under 20°, acute radiuses below 0.5 mm and more.

Moreover, one of the most negative aspects of such a system consists in that the assembly of the tablets should be performed while leaving a certain air gap between the various tablets, and this to permit an easy descent thereof into the cup. If the gap is excessive, however, the lines may be irregular, while if such a space is reduced, the tablets could rub against one another during the descending step and then create colour invasions or coloured overflows between one tablet and the other.

If the formulas of the single tablets are different from one another, it is highly easy for the two joined surfaces to have a particularly unappealing step in the final compacting step due to the bonding of two or more products the density, consistency and formulating features of which are sometimes very different.

This almost applies to the poured products, for which the technology, which may currently allow tablet poured products to be made in the same container, provides pouring different products by means of fusers within respective spaces of a cup or a final container which are defined by one or more separating bodies, insertable and removable, and variously shaped. The poured products are allowed to cool until solidification, then the separator is extracted and repositioned to permit the pouring and solidifying operation to be repeated up to the last space available.

The separators inserted inside the container to define the spaces of the single tablets and give them the shape wanted are generally made of metal, but they may also be made of plastic or other material. The fundamental requirement of the separators is that they allow the product to be detached from their walls without problems after solidification.

Thereby, poured products may be obtained in the same cup or container, consisting of a certain number of colours and shapes, normally from a minimum of two to a maximum of five and more, perfectly joined with one another.

The most encountered problems by using such a technique are substantially related to the high production costs of the separators, which use particularly elaborate and costly production techniques, as well as the appearance results of the final product which, in addition to always and only being flat, without any relief or volume, is not always uniform between the various parts and often has level differences between one tablet and the other.

SUMMARY

It was the object of the present invention to provide a process for preparing tablet cosmetic products which avoids the aforementioned problems.

Such an object is achieved by a process which provides the use of a pouring container equipped with partitions arranged on the base of the container itself.

With the new invention, the partitions may directly be made together with the pouring container, with a significant equipment cost reduction.

Another positive aspect is that the number of shapes which are possible to be obtained becomes very greater, as a production technique may be used for the pouring containers by means of injecting plastics which permits to reach thicknesses even within a few tenths of a millimetre, without particular shape restrictions and various templates.

The separating partitions may either be fixed, i.e. directly made together with the pouring container, and movable, i.e. removably positioned on a fixed base, e.g. inserted into suitable slots of the containers.

The choice to use fixed or movable partitions may be dictated by the fact that some products could adhere to the partition in the drying step, or by the fact of having problems in directly shaping them in the moulding step.

In general, the fixed partitions will be made of metal, but alternatively other materials may also be used, provided that their mechanical resistance is particularly high.

DETAILED DESCRIPTION

An example diagram of the production process according to the present invention which uses pouring containers equipped with fixed separating partitions is briefly illustrated in FIGS. 1-4.

Figure 1:
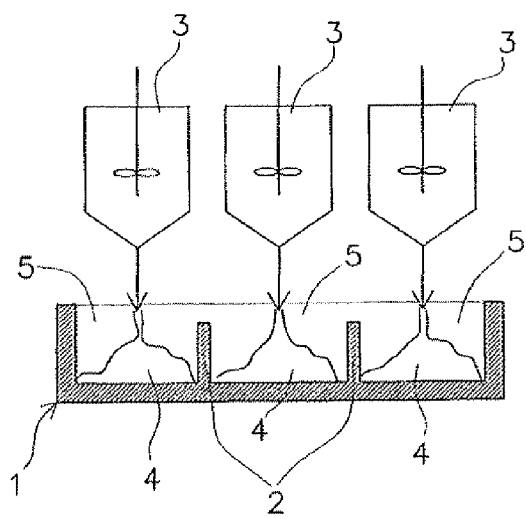
FIGS. 1-4 show an exemplary production process using pouring containers equipped with fixed separating partitions according to the present invention.

FIG. 1 shows a shaped container 1, equipped with fixed partitions 2 arranged on the base thereof, which is filled with equal or different coloured cosmetic compounds 4 in the form of a slurry, or in semi-liquid state, in the single spaces 5 defined by the partitions 2.

Partitions 2 are short with respect to the total depth of the container.

The dosage of the various products in the single spaces 5 occurs by using dosing devices 3.

Such an operation may occur either by means of a single step, i.e. by sequentially dosing the single colours up to the upper edge of the partition, except the last which will be over-dosed up to surmounting all the others previously dosed, until forming a single body with one another, or simultaneously, so as to have an immediate bonding between the various products dosed.

The dosing devices used may be volumetric, with gears, under pressure or however any suitable system could be used for filling a semi-liquid product into a cavity, precisely and without alternations of the product dosed.

Hot dosage of the product may be performed, with temperatures from 50° to 100° C., as well as cold dosage, and the dosed product may consist of powders dispersed in a water carrier, or the carrier may consist of water and organic solvents.

The dosable product may also consist of a heat-pourable anhydrous product, e.g. multi-purpose, lip red, solid foundations, etc.

Figure 2:
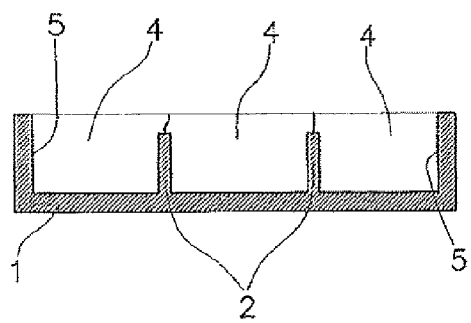

FIG. 2 shows container 1 equipped with partitions 2, filled with three different cosmetic products 4 into the single spaces 5, after product solidification, ready to be put to oven-dry, if the product contained is a slurry dispersed in a water medium, or to be cooled to complete solidification, if the product consists of a heat-pourable anhydrous cosmetic.

The container intended to receive the product, both is a water and in a casting anhydrous slurry, generally consists of injection-moulded plastics, such as SAN, ABS, SAN+ABS, PP or others.

The container may be smooth or with reliefs and shapes of various height and size.

Bi-component resins such as PMMA, polyurethane resins and the like, or polymerisable bi-component fluid silicones may also be used to make it.

Figure 3:
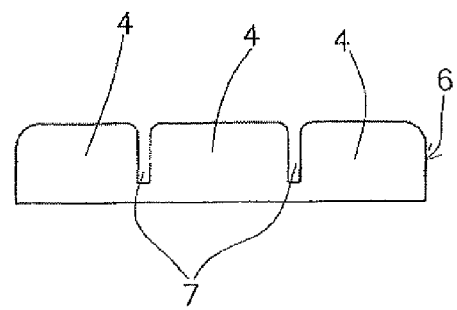
Figure 4:
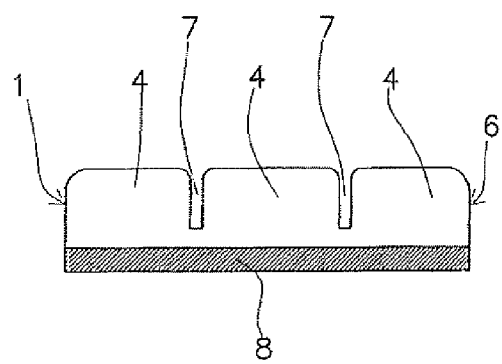

In FIG. 3, the product indicated by 6 as a whole is in its final form, upon solidification or drying, where 4 are the single coloured tablets dosed in the respective cavities, separated from one another by slots 7 which result from the presence of the separating partitions 2, upon the extraction from container 1.

A support layer 8 made of rigid material may also be placed on the base of the solidified product in order to keep the piece as rigid as possible, and promote its sticking in the final kit.

Such a support, generally consisting of plastics, ceramic, baked clay, plastic mesh, or anything similar, is stuck to the product when solidifying it.

The advantages resulting from the new invention are apparent from the aforementioned description: a strong reduction of the equipment costs, due to the fact that complex and costly metal equipment should no longer be made which should then be inserted into the container. With this system, the separation of the spaces intended for the single product tablets is directly carried out in a single step, which is that of preparing the pouring container.

Another significant advantage is the reduction of the production costs, because, if the dosages occurred in a single step with the traditional systems resulting in a great expenditure of appointed personnel, with the present invention the dosage of more colours simultaneously occurs in a single step, thus greatly reducing the use of personnel appointed to production.

With regards to the aesthetic appearance, the present invention totally suppresses all the superficial defects on the separation lines among various tablets, such as invasions of various colours in the different seats, colour overflows on the separation lines, steps of different level between the different tablets. Indeed, as the product is poured overturned with respect to the traditional systems, the form leaving the process is exactly identical to that of the bottom wall of the respective cavity of the pouring container.

Moreover, by creating a small detachment among the various tablets, the partitions cancel all possibilities of colour invasion and contamination between one tablet and the other.

Figure 5:
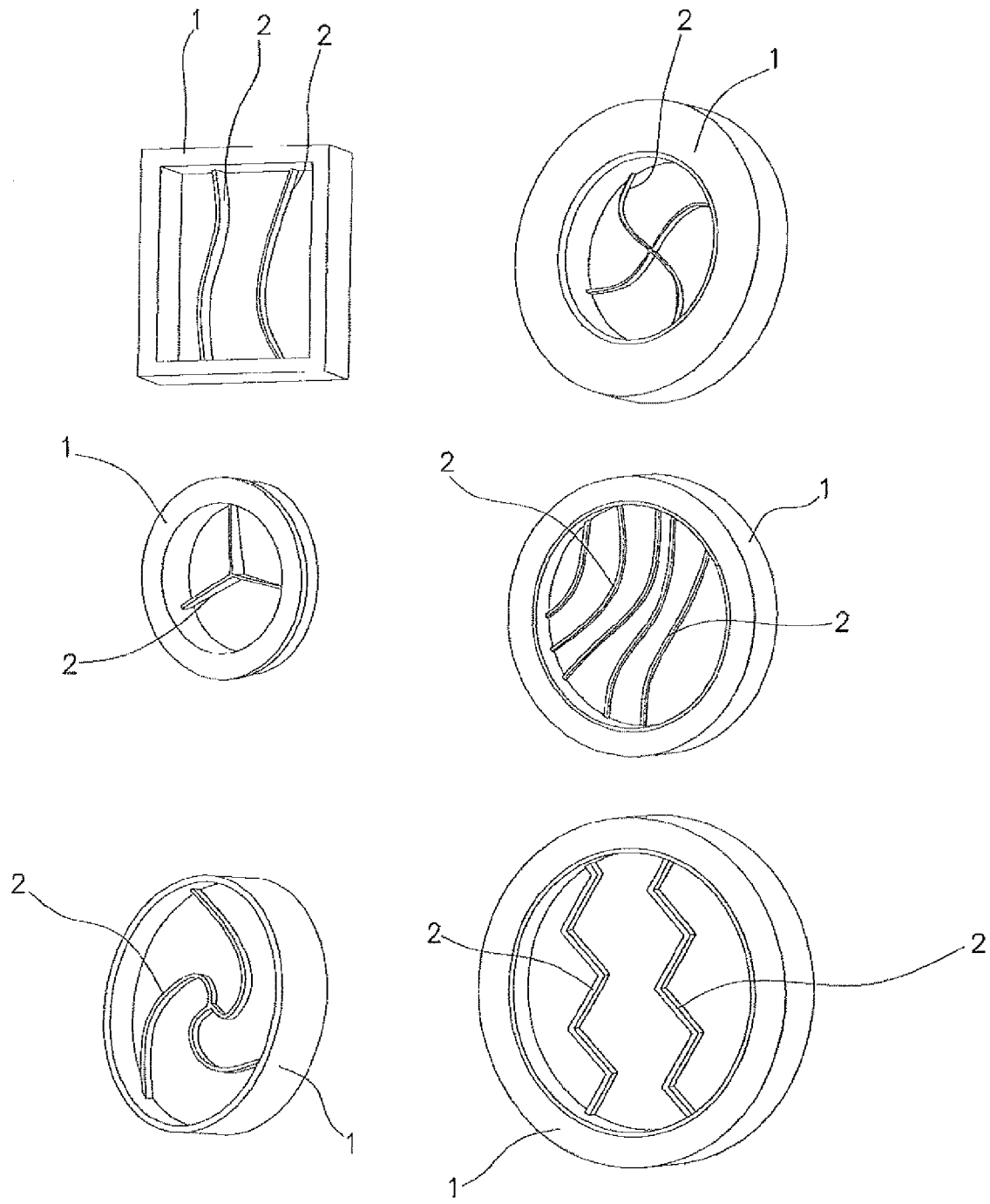
FIG. 5 shows containers of various shapes internally equipped with fixed partitions.

By way of example, FIG. 5 shows containers of various shapes internally equipped with fixed partitions.

As already mentioned, alternatively to the fixed partitions, the same partitions may be removable by extraction from the base of the pouring container.

Figure 6:
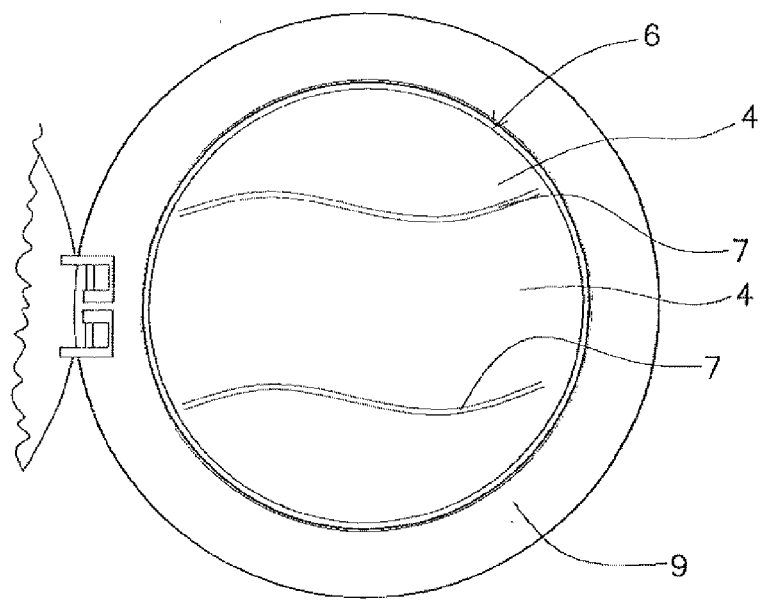
FIGS. 6 and 7 show exemplary packages or kits of cosmetic products in tablets obtained by means of the process according to the present invention.
Figure 7:
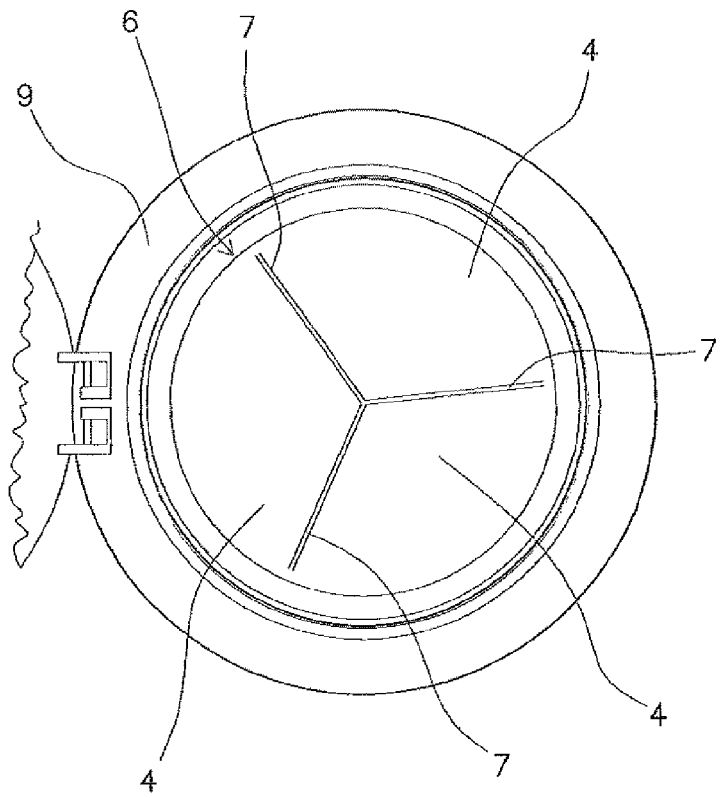

FIGS. 6 and 7 show non-limiting examples of packages or kits 9 of cosmetic products in tablets obtained by means of the process according to the present invention.

The invention claimed is:

1. A process comprising:
    separately pouring a plurality of cosmetic compounds into respective adjacent spaces of an upwardly open moulding-pressed container,
        wherein each of the plurality of cosmetic compounds has a form selected from the group consisting of a slurry and a semi-fluid,
        wherein the upwardly open moulding-pressed container has a side wall and a bottom base and provided with internal partitions rigidly fixed to said bottom base and extending upwardly therefrom to define said adjacent spaces,
        wherein the internal partitions have a height lower than the depth of the moulding container, wherein the pouring is carried out such that at least one of the plurality of cosmetic compounds surmounts all the partitions of the container so as to form an upper bonding surface;

solidifying the plurality of poured compounds to form a single cosmetic product, wherein the single cosmetic product has an upper flat layer from which adjacent tablets corresponding to the separately poured compounds extend downwardly;

extracting the single solidified product from the moulding container;

overturning the extracted solidified product;

introducing the overturned solidified product into a final distinct package, wherein the partitions are permanently fixed at the bottom of the container.

2. The process according to claim 1, wherein the plurality of cosmetic compounds are powders dispersed in a liquid carrier selected from the group consisting of water and an organic solvent.

3. The process according to claim 1, wherein the plurality of cosmetic compounds are heat-pourable anhydrous products.

4. The process according to claim 1, wherein the unique tablet cosmetic product is solidified and oven-dried.

5. The process according to claim 1, wherein the unique tablet cosmetic product is solidified by cooling.

6. The process according to claim 4, further comprising applying and gluing a layer of rigid material to the unique tablet cosmetic product at the moment of the unique tablet cosmetic product's solidification.

7. A process comprising:

separately pouring a plurality of cosmetic compounds into respective adjacent spaces of an upwardly open moulding-pressed container, wherein each of the plurality of cosmetic compounds has a form selected from the group consisting of a slurry and a semi-fluid, wherein the upwardly open moulding-pressed container has a side wall and a bottom base and provided with internal partitions rigidly fixed to said bottom base and extending upwardly therefrom to define said adjacent spaces, wherein the internal partitions have a height lower than the depth of the moulding container, wherein the pouring is carried out such that at least one of the plurality of cosmetic compounds surmounts all the partitions of the container so as to form an upper bonding surface;

solidifying the plurality of poured compounds to form a single cosmetic product, wherein the single cosmetic product has an upper flat layer from which adjacent tablets corresponding to the separately poured compounds extend downwardly;

extracting the single solidified product from the moulding container;

overturning the extracted solidified product;

introducing the overturned solidified product into a final distinct package, wherein the partitions are irremovably fixed to the container.

8. The process according to claim 7, wherein the plurality of cosmetic compounds are powders dispersed in a liquid carrier selected from the group consisting of water and an organic solvent.

9. The process according to claim 7, wherein the plurality of cosmetic compounds are heat-pourable anhydrous products.

10. The process according to claim 7, wherein the unique tablet cosmetic product is solidified and oven-dried.

11. The process according to claim 7, wherein the unique tablet cosmetic product is solidified by cooling.

12. The process according to claim 10, further comprising applying and gluing a layer of rigid material to the unique tablet cosmetic product at the moment of the unique tablet cosmetic product's solidification.

* * * * *